United States Patent [19]

Dobrogowski et al.

[11] Patent Number: 5,025,811
[45] Date of Patent: Jun. 25, 1991

[54] METHOD FOR FOCAL DESTRUCTION OF EYE TISSUE BY ELECTROABLATION

[76] Inventors: Michael J. Dobrogowski, #235, 2025 W. 42nd Ave., Vancouver, 2B5; Mark A. Latina, 71 Paddock La., No. Andover, Mass. 01845

[21] Appl. No.: 480,742

[22] Filed: Feb. 16, 1990

[51] Int. Cl.$^5$ ............................................. A61N 3/04
[52] U.S. Cl. .................................... 128/898; 128/362; 128/783; 128/800; 606/41; 606/49; 604/20
[58] Field of Search ............... 128/362, 399, 400, 401, 128/362, 783, 784, 786, 800, 804, 898; 606/4, 27, 31, 32, 34, 40, 41, 49, 50, 45, 33; 604/19-22

[56] References Cited

U.S. PATENT DOCUMENTS 4,449,528 5/1984 Auth et al. .............................. 606/31
4,564,016 1/1986 Maurice et al. ...................... 128/645

OTHER PUBLICATIONS

Berens et al. (1949) J. Trans. Am. Opthamol. Soc. 47:364–382.
Maurice (1983) Ocular Inflam. Ther. 1:97–102.
Fishman et al. (1984) Invest. Opthalmol. Vis. Sci. 25:343–345.
Hughes et al. (1984) Arch. Opthalmol. 102:1825–1829.
Barza et al. (1986) Opthalmol. 93:133–139.
Maurice (1986) Opthalmol. 93:128–132.
Choi et al. (1988) J. Ocular Pharmacol. 4:153–164.
Grossman et al. (1989) Opthalmol. 96:724–729.

Primary Examiner—Stephen C. Pellegrino
Assistant Examiner—David Shay
Attorney, Agent, or Firm—Lahive & Cockfield

[57] ABSTRACT

A non-invasive method for focal transcleral destruction of living human eye tissue. The method includes providing a conical-shaped probe, filled with a neutral saline solution and having inserted therein an electrode connected to the positive terminal of a constant current supply. The narrow aperture ends of the probe is lowered onto the conjunctiva overlying the target tissue, in about 20-30 locations with a current in the range from about 3.0–4.0 milliamps for about 30 seconds to 5 minutes at each location.

15 Claims, 2 Drawing Sheets

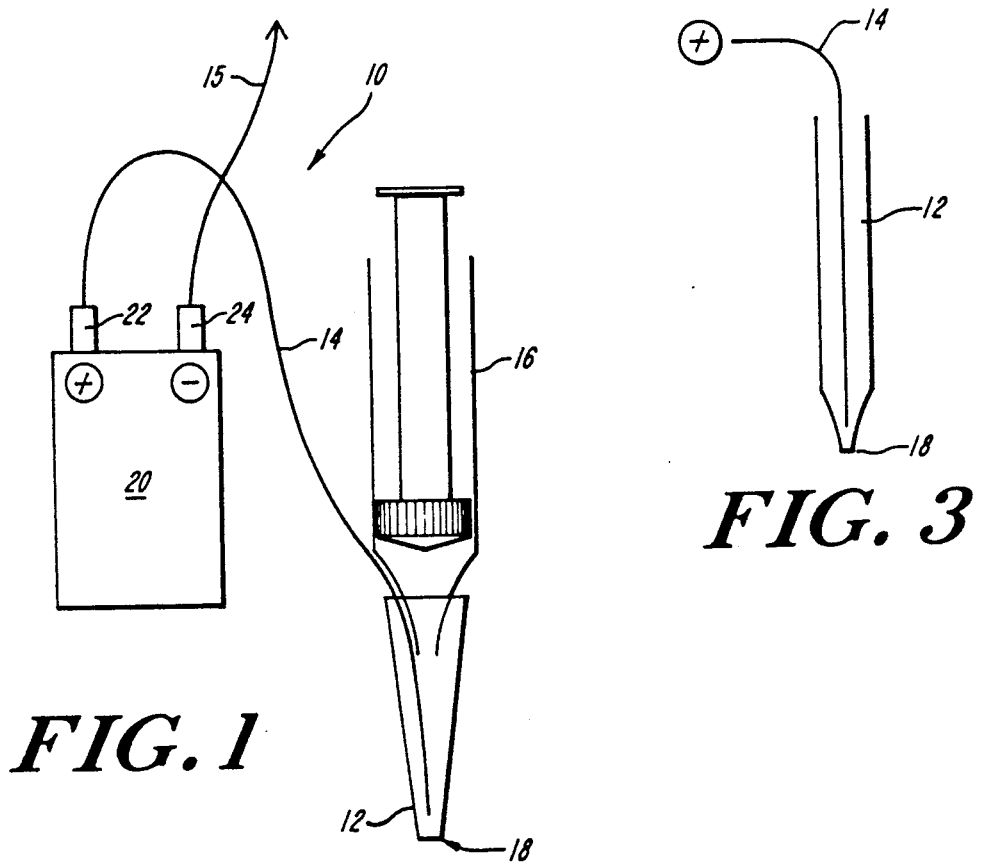
*FIG. 1*
*FIG. 3*
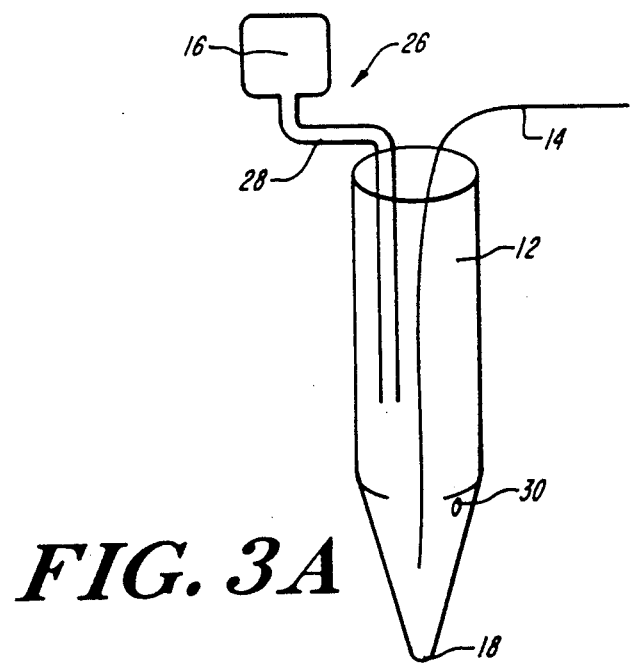
*FIG. 3A*

METHOD FOR FOCAL DESTRUCTION OF EYE TISSUE BY ELECTROABLATION

BACKGROUND

This invention relates to non-invasive methods for ablating eye tissue using an electric current delivered transclerally. A specific application of this invention includes reduction of intraocular pressure by focal destruction of the ciliary process.

Glaucoma is a potentially debilitating disease of the eye in which the intraocular pressure within the eye rises above normal levels. Glaucoma is generally treated by a surgical procedure where a small hole is introduced through the sclera, which is the outer coating of the eye, to allow fluid within the eye to drain into the subconjunctival space, between the conjunctiva and the sclera.

Cycloablation, which is a destruction of the ciliary body, is another method by which an ophthamologist can reduce intraocular pressure. The ciliary processes are involved in the production of fluid within the eye. Thus, by destroying the ciliary processes, aqueous production is reduced. Cycloablation is primarily prescribed for advanced glaucoma patients with poor vision.

At present there are a number of cycloablative or cyclodestructive procedures. These procedures include cyclocryotherapy, transscleral Nd:YAG laser cycloablation, therapeutic ultrasound, cyclodiathermy, and transpupillary argon ciliary process photoablation. There can be a significant post-treatment pressure spike, marked intraocular inflammation and unpredictability associated with each of these methods. The degree of unpredictability is such that in some cases phthisis bulbi ensues. A preferred technique would be one which is more predictable, and associated with minimal inflammation.

Iontophoresis, which is a means of introducing drugs in ionized form into tissues by means of electric current, has become increasingly popular in North America over the past several years. Its applications range from dye-enhanced ablation with laser sclerotomies to the experimental treatment of keratitis and endophthalmitis using antibiotics. Most research concerning the use of iontophoresis utilizes the method as a non-invasive mode of introducing effective levels of drugs to various regions of the eye, such as the vitreous humor. As a mode of drug administration, the prior art teaches regulation of current, probe diameter and time to avoid tissue damage. See, for example, U.S. Pat. No. 4,564,016 to Maurice et al.

One reference, Berens, Sheppard and Duel, *Cycloelectrolysis for Glaucoma.* J. Trans. Am. Opthamol. Soc. 47:364-382 (1949), describes the use of electricity to destroy the ciliary body. The technique described involves inserting a needle directly into the ciliary body. In a majority of cases, dissection of the conjunctiva was required and 50-75 punctures were recommended. While such invasive means alleviate ocular pressure, complications such as infections may arise which are related to the procedure.

Thus, there is a need for a non-invasive means for relieving intraocular pressure and an efficient, less traumatic means for ablating eye tissue.

SUMMARY OF THE INVENTION

The invention features a method for ablating eye tissue, including a non-invasive method for reducing intraocular pressure by focal destruction of the ciliary body of a human eye using an electric current which is delivered transclerally by means of a probe-electrode.

The method of the invention consists of placing a probe upon the conjunctiva overlying the ciliary body or other similar structure of a human eye. The probe is non-conductive and conical. It has an aperture of sufficient size at one distal end to receive both a conductive electrode and a means for filling the probe with a neutral salt solution. At the other proximal end of the probe is an aperture of predetermined size to focus the amount of current flowing through the probe onto the conjunctiva. The aperture size may be in the range of from about 200 micrometers to 2000 micrometers, preferably in the range of from 300-600 microns.

The conductive electrode contained in the probe is connected to the positive terminal of a constant current supply. The negative terminal of the constant current supply is grounded to the patient via either a lid speculum or an EKG electrode placed on the patient's face. A syringe or tube may be used to fill the probe with a neutral solution, such as phosphate buffered saline or balanced salt solution.

The proximal end of the probe is placed on the conjunctiva proximate to the ciliary body, or proximate another target tissue of the patient's eye. A current in the range of from about 1.5 milliamps to about 8.0 milliamps, preferably in the range of from 3.0-4.0 milliamps, is passed through the conducting electrode onto the scleral surface. The current is allowed to pass for a duration in the range of about 30 seconds to 5 minutes at each probe location. Multiple repeated placements may be made on any one eye. The probe is placed 20-30 different places around the circumference of the eye encircling the limbus. Points along the 3 O'clock and 9 O'clock positions are avoided to prevent damaging any underlying ciliary nerves.

It is an object of this invention to provide a relatively less traumatic method for ablating eye tissue.

It is another object of this invention to provide a method for relieving intraocular pressure which minimizes inflammatory response while maximizing the amount and duration of intraocular pressure reduction.

It is another object of this invention to provide a reliable and more predictable method for relieving intraocular pressure and ablating eye tissue.

It is another object of this invention to provide a non-invasive method of relieving intraocular pressure and otherwise ablating eye tissue so as to avoid post-surgical complications, such as infections.

Other objects, features, and advantages of the invention will be apparent from the following description of the preferred embodiments therof, and from the claims.

DESCRIPTION OF THE PREFERRED EMBODIMENT

The drawings will first briefly be described.

Drawings

FIG. 1 is a diagrammatic representation of the electroablation system of the invention.

FIG. 3 is a diagrammatic representation of the electroablation system of the invention having a filled glass pipet as a probe.

FIG. 3a is a diagrammatic representation of an alternate form of the electroablation system of the invention.

Structure

Figure 2:
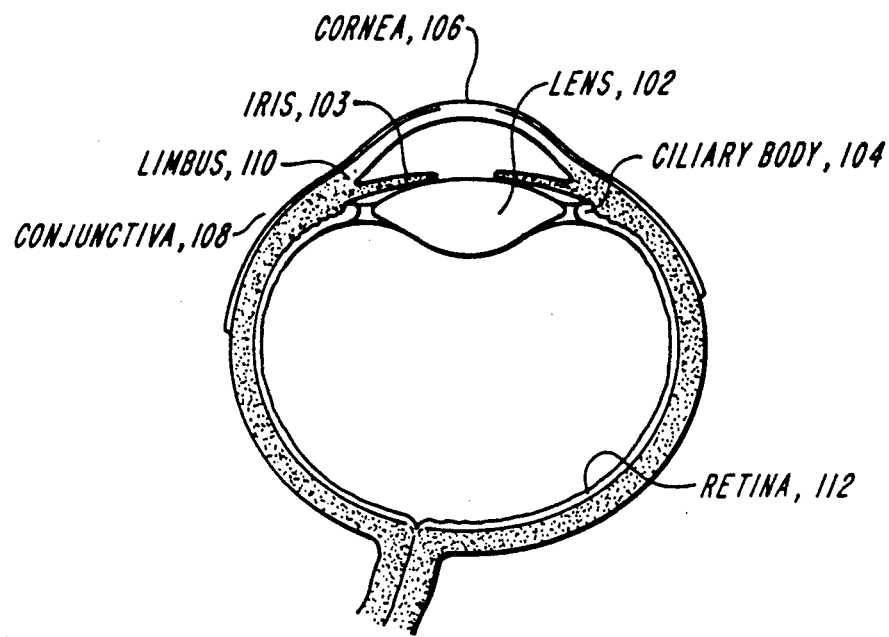
FIG. 2 is a cross-sectional view of a human eye.

Referring to FIGS. 1 and 2, an electroablation system 10 includes a probe 12, filled with a neutral solution, and having an electrode 14 connected to a constant current supply 20. The system consists of repeatedly placing the probe 12 on the conjunctiva 108 of a human eye 100 proximate to a ciliary body 104 or other target eye tissue such that electrical current passes from the current supply 20 through the probe 12 to focally destroy the underlying ciliary body 104 or target eye tissue.

The probe 12 is generally conical-shaped and hollow, having one distal end large enough to receive an electrode 14 and a filling means 16 for the filling solution. The other proximal end of the probe 12 is more narrow, having an aperture 18 of predetermined diameter. The probe 12 is made of any non-conductive material, such as a plastic or glass. Alternatively, as shown in FIG. 3, the probe 12 may be made from a glass pasteur pipet which has been heated and pulled to have an appropriate aperture size. The probe may be reusable, or disposable and should be capable of being sterilized, or autoclavable.

The electrode 14 is made of stainless steel, platinum, or any other suitable conductive material. One end of the electrode 14 is connected to the positive terminal 22 of a constant current supply 20. The other end is inserted into the wide distal end of the probe 12, and suspended in the filling solution. The electrode 14 does not extend through the probe aperture 18, but remains suspended in the body of the probe 12 above the aperture 18.

A ground electrode 15 is attached to the negative terminal 24 of the constant current supply 20. The ground electrode 15 is made of stainless steel, platinum, or a similar conductive material. The patient may be used to electrically ground the device by using an electrocardiogram (EKG) probe, a lid speculum, or any other suitable conductive surface or structure which is in contact with the patient.

The aperture 18 size is determined by the desired size of the destructed area. The aperture size may vary in the range of from about 200 micrometers to about 2 millimeters, preferably in the range of about 300-600 microns. The proximal end having aperture 18 of the probe 12 is placed directly on the conjunctiva 108 overlying the ciliary body 104, or other target eye tissue, approximately 0.5 to 2.0 millimeters from the limbus 110 of the patient's eye. Thus, the size and shape of the aperture 18 may be modified to achieved a desired amount of destruction to the underlying ciliary body 104. Such a device may also effectively be used to destroy the retina.

The probe 12 is filled with a neutral solution, such as saline. In one aspect, phosphate buffered saline is used as a neutral filling solution. In another aspect, specific agents directly affecting aqueous production or aqueous outflow may be utilized. Such agents include carbonic anhydrase inhibitors. A filling means 16 may be a syringe or tube, and is used to fill the probe with the saline solution. If a syringe is used, it may be attached to a flow pump, which delivers a constant flow of solution at a predetermined flow rate. Alternatively, a tube may be used, similarly attached to a pump having a predetermined flow rate.

In another aspect, as shown in FIG. 3, the probe 12 may be pre-filled. If the probe 12 is made of glass, as with a pasteur pipet, electrons may pass through the enclosed glass tip. Thus, after the pipet is heated and pulled to make the desired aperture diameter, the pipet is back-filled with saline solution.

In yet another aspect of the invention, as shown in FIG. 3A, the probe 12 may have means for providing a constant infusion of saline (e.g. balanced salt solution). Such an infusion system 26 keeps fresh saline solution flowing into the probe 12, via an infusion tube 28, and out of the probe 12 via an infusion aperture 30. The constant flow also assures that the pH of the solution within the probe 12 remains relatively constant.

Figure 4:
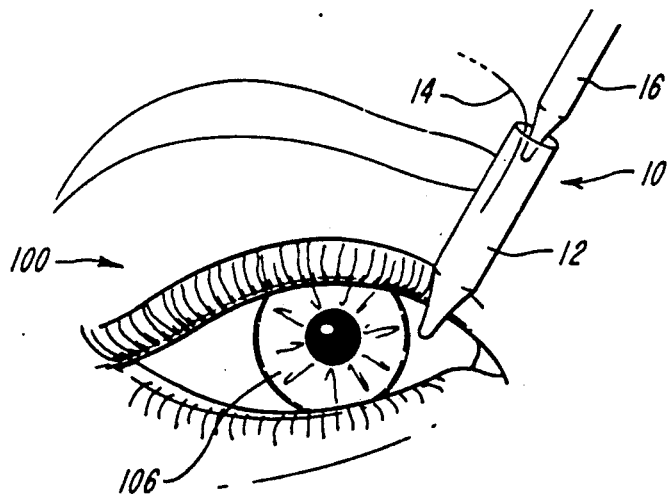
FIG. 4 shows the manner in which the electroablation system of the invention is applied to a human eye.

FIG. 2 is a cross-sectional view of a human eye showing the relative location of the iris 103, ciliary bodies 104, conjunctiva 108, cornea 106, and lens 102. The method of this invention involves non-invasive focal destruction of one or both ciliary processes and/or the retina 112. The system 10 is used by lowering the proximal end of probe 12 onto a patient's eye, as shown in FIG. 4, by mechanical or manual means. A stereotaxic harness may be used which would allow accurate placement of the probe 12 on a specific location of the eye. Mechanical devices which allow for horizontal, vertical and Z-axis movement of the probe 12 would be optimal. Alternatively, the probe may be hand-held, having a constant current and filling solution flow, and touched on the eye using visual aids such as a head-mount monocular or binocular scope. It is also possible to have a computer-controlled system which would move the probe 12 to preselected locations, lower the probe, time the duration of contact of the probe 12 to the conjunctiva 108, and monitor the amount of current. It is important that the aperture 18 rests on the surface of the eye, and does not penetrate or otherwise destroy the integrity of the surface to maintain a reduced inflammatory response.

For electrocycloablation of a ciliary body 104, the probe is placed posterior to the edge of the cornea 106 overlying the ciliary body 104, as shown in FIG. 4. For ablation of other eye tissue, such as the retina 112, the probe is similarly placed on the conjunctiva 103 overlying the appropriate tissue to be ablated. For retinal ablation, this would mean placing the probe further posterior to the edge of the cornea 106.

Once the probe 12 is placed on a patient's eye, a current is passed along the electrode 14 at a range of from about 1.5 milliamps to about 8.0 milliamps, preferably from about 3.0-4.0 milliamps. The 3.0-4.0 milliamp range is the most effective range for focal destruction of the ciliary body, with the least side effects. The current is passed for a duration of from about 30-90 seconds at each location. The current may be passed for a duration of 30 seconds to five minutes, depending upon the tissue to be ablated. The probe 12 is placed at about 20 to 30 locations around the circumference of the eye, avoiding placement along the 3 O'clock to 9 O'clock axis. Generally, the ciliary nerves terminate at and radiate from or near these positions. By avoiding probe placement along this axis, uncontrolled damage to the optic nerves may be prevented.

The parameters suitable for use of the above electrocycloablation system are chosen to minimize inflammatory response and maximize the amount and duration of intraocular pressure reduction. Generally, an average intraocular pressure reduction of about 40 percent at three days may be achieved. There is a minimal inflammatory response, and the pressure reduction persists over a period of approximately two weeks.

Method

There follows an example of use of the above electrocycloablation system for intraocular pressure reduction. This example is not limiting to the invention. In this example, parameters were chosen to achieve a 40 percent pressure reduction.

Prior to treatment with the system 10, the eye is treated with a local retrobulbar anesthesia of a 2% xylocaine 0.75% marcaine solution. A lid speculum is inserted between the eyelid and eye to be treated, to expose the eyeball. The patient is grounded by attaching the negative electrode to the flow of 0.9% saline solution is established over the eyeball from an intravenous bottle and flow system.

To perform the ablation, the probe 12 is placed on the conjunctiva 108 overlying the ciliary body 104 or retina 112 to be ablated. For cycloablation, the probe is placed approximately 2 millimeters from the limbus 110. The current is turned on via a foot switch and gradually increased to 3-4 milliamps. This current is then maintained at each location for 30-90 seconds, for cycloablation. The exact time may be maintained by an automatic timer. The process is repeated approximately 20 times, around the circumference of the eye, exclusive of the 3 O'clock and 9 O'clock positions.

Following application of the probe 12, the eye is irrigated with saline solution. A topical application of a 1% atropine/1% prednisilone acetate plus antibiotic solution is postoperatively applied to the eye. A subconjunctival steroid may also be applied. A patch is used to cover the eye during healing.

Other embodiments are within the following claims.

What we claim is:

1. A non-invasive method for focal non-invasive transcleral destruction of living human eye tissue, comprising the steps of:
   (a) providing a hollow probe having a distal end and a proximal end;
   and, at said distal end a first aperture to receive a conductive electrode and means for filling said probe with a neutral solution;
   and, at said proximal end a second aperture of predetermined diameter;
   (b) connecting said conductive electrode to a constant current supply having a positive terminal and a negative terminal;
   (c) filling said probe with a neutral solution using said filling means;
   (d) adjusting said constant current supply to a current in the range of between about 1.5 milliamps to about 8.0 milliamps;
   (e) repeated placement of said proximal end of said probe onto a scleral surface of a human eye proximate to target eye tissue at a plurality of locations; and
   (f) each of said placement remains for a predetermined duration.

2. The method of claim 1 further comprising the step of avoiding said probe placement on said human eye at 3 O'clock and 9 O'clock positions.

3. The method of claim 2 wherein said plurality of locations of said probe is in the range of from about 20 to 30 times.

4. The method of claim 1 wherein said neutral solution is a saline solution.

5. The method of claim 4 wherein said saline solution is a balanced salt solution.

6. The method of claim 1 for treatment of intraocular pressure wherein said target eye tissue is a ciliary body.

7. The method of claim 6 wherein:
   said duration of each probe placement is in the range of about 30 seconds to about 90 seconds; and
   said probe is placed in a predetermined location on said living eye overlying said ciliary body.

8. The method of claim 1 wherein said duration of each placement of said probe onto said scleral surface is in the range of from about 30 seconds to about 5 minutes.

9. The method of claim 1 further comprising the steps of connecting said conductive electrode to said positive terminal of said constant current supply and connecting said negative terminal to a ground.

10. The method of claim 1 wherein step (c) further comprises filling said probe using a syringe as said filling means.

11. The method of claim 1 wherein step (c) further comprises providing constant flow of said neutral solution through said probe.

12. The method of claim 1 wherein the diameter of said second aperture is in the range of from about 200 micrometers to 2000 micrometers.

13. The method of claim 1 wherein the diameter of said second aperture is in the range of from about 300 microns to about 600 microns.

14. The method of claim 1 wherein said current is from about 3.0 milliamps to about 4.0 milliamps.

15. The method of claim 1 wherein said target eye tissue is a retina.

* * * * *